(12) United States Patent
Anderson et al.

(10) Patent No.: US 6,974,879 B2
(45) Date of Patent: Dec. 13, 2005

(54) PROCESS FOR PREPARING SINGLE ENANTIOMERS OF 5,5,5,5',5',5'-HEXAFLUOROLEUCINE AND PROTECTED ANALOGS

(75) Inventors: James T. Anderson, Shaker Heights, OH (US); Edward Neil Marsh, Ann Arbor, MI (US); Peter Laurence Toogood, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 5 days.

(21) Appl. No.: 10/910,236

(22) Filed: Aug. 3, 2004

(65) Prior Publication Data

US 2005/0020683 A1 Jan. 27, 2005

Related U.S. Application Data

(62) Division of application No. 10/663,311, filed on Sep. 16, 2003, now Pat. No. 6,787,664.
(60) Provisional application No. 60/411,489, filed on Sep. 17, 2002.

(51) Int. Cl.$^7$ ............................................. C07C 229/00
(52) U.S. Cl. ...................... 560/172; 560/155; 560/170; 562/574
(58) Field of Search ................................. 560/172, 155, 560/170, 129, 179, 184; 562/574, 579, 586, 602, 605; 564/503, 510

(56) References Cited

PUBLICATIONS

Anderson et al., A Short and Efficient Synthesis of L–5,5,5,5',5',5'-hexafluoroleucine from N–Cbz–L–Serine, Organic Letters (2002), 4(24), 4281–428.*
Bravo et al., A cycloadditive route to trifluoromethyl–substituted amino alcohols, Tetrahedron (1992), 48(44), 9775–88 (Chemical Abstracts online abstract).*
Marsh, E.N.G., et al, "Towards the nonstick egg: designing fluorous proteins", Chem. Biol., (2000), pp. R153–157, vol. 7.
Horvath, I., et al., "Fluorous Biphase Chemistry", Acc. Chem. Res., (1998), pp. 641–650, vol. 31.
Luo, Z.Y., et al, "Fluorous Mixture Synthesis: A Fluorous–Tagging Strategy for the Synthesis and Separation of Mixtures of Organic Compounds", Science, (2001), p. 1766, vol. 291.
Tang, Y. et al., "Stabilization of Coiled–Coil Peptide Domains by Introduction of Trifluoroleucine", Biochemistry, (2001), pp. 2790–2796, vol. 40.
Lazar, J., "Fluorinated Analogs of Leucine, Methionine, and Valine", J. Med. Chem., (1968), pp. 138–140, vol. 11.
Zhang, C., et al, "Asymmetric Synthesis of (S)–5,5,5,5',5',5'-Hexafluoroleucine", Helv. Chem. Acta, (1998), pp. 174–181, vol. 81.
Xing, X. et al, "A Novel Synthesis of Enantiomerically Pure 5,5,5,5',5',5'–Hexafluoroleucine", Org. Lett., (2001), pp. 1285–1286, vol. 3, No. 9.
Barton, D.H.R., et al, "A New Method for the Deoxygenation of Secondary Alcohols", J. Chem. Soc. Perkin Trans. 1, (1975), pp. 1574–1585, vol. 1.
Robins, M.J., "Smooth and Efficient Deoxygenation of Secondary Alcohols. A general Procedure for the Conversion of Ribonucleosides to 2'–Deoxynucleosides", J. Am. Chem. Soc.,m (1981), pp. 932–933, vol. 103.
Robins, M.J., "Nucleic Acid Related Compounds. 42. A General Procedure for the Efficient Deoxygenation of Secondary Alcohols. Regiospecific and Stereoselective Conversion of Ribonucleosides to 2'–Deoxynucleosides", J. Am. Chem. Soc., (1983), pp. 4059–4065, vol. 105.
Dolan, S. C., et al, "A New Method for the Deoxygenation of Tertiary and Secondary Alcohols", J. Chem. Soc. Chem. Commun., (1985), pp. 1588–1589.

* cited by examiner

Primary Examiner—Johann Richter
Assistant Examiner—Karl Puttlitz
(74) Attorney, Agent, or Firm—Matthew J. Russo; Charles W. Ashbrook

(57) ABSTRACT

A process for synthesizing L and D-5,5,5,5',5',5'-hexafluoroleucine and protected analogs is disclosed. These compounds have utility in the preparation of fluorous peptides and proteins, which display interesting and unusual properties including strong self-association and an affinity for lipid bilayers.

6 Claims, No Drawings

PROCESS FOR PREPARING SINGLE ENANTIOMERS OF 5,5,5,5',5',5'-HEXAFLUOROLEUCINE AND PROTECTED ANALOGS

CROSS-REFERENCE TO RELATED APPLICATIONS

This application is a division of commonly assigned U.S. application Ser. No. 10/663,311, filed Sep. 16, 2003, now U.S. Pat. No. 6,787,664 which claims the benefit of U.S. Provisional Application No. 60/411,489, filed Sep. 17, 2002.

BACKGROUND OF THE INVENTION

1. Field of Invention

This invention relates to a method of preparing L- and D-5,5,5,5',5',5'-hexafluoroleucine and protected analogs thereof, including compounds having a protected amino functional group, compounds having a protected carboxy functional group, and compounds having protected amino and carboxy functional groups. These compounds are useful for the preparation of fluorous peptides and proteins.

2. Discussion

Hexafluoroleucine is of considerable interest as an extensively fluorinated analog of leucine that may be used as a building block in the design of fluorous proteins and peptides (E. N. G. Marsh, 7 *Chem. Biol.* R153 (2000)). Fluorocarbons have long been known for their chemical inertness, and their unique physicochemical properties have found industrial and medical uses as fire retardants, refrigerants, anesthetics and biologically inert polymers. The tendency of extensively fluorinated, or fluorous, organic molecules to partition into perfluorinated solvents has been exploited in organic synthesis to facilitate purification of products from reaction mixtures (I. T. Horvath, 31 *Acc. Chem. Res.* 641 (1998); Z. Y. Luo et al., 291 *Science* 1766 (2001)).

Recently, there has been much interest in whether the novel properties exhibited by fluorocarbon polymers can be exploited in the design of biological macromolecules. Extensively fluorinated analogs of hydrophobic amino acids, when substituted into proteins and peptides, pack into the hydrophobic core of the protein to produce proteins that combine novel physicochemical properties with biological activity (Y. Tang et al., 40 *Biochemistry* 2790 (2001)). Peptides designed to form dimeric coiled-coil structures based on the "leucine zipper" domain of the transcription factor GCN4, or de-novo designed sequences that incorporate (4R, 4S)-L-trifluoroleucine, (3R, 3S)-L-trifluorovaline or L-hexafluoroleucine, display increased stability, enhanced self association and stronger receptor-ligand binding than their non-fluorinated counterparts.

Hexafluoroleucine (hFLeu) is a highly fluorinated analog of leucine, an amino acid that plays an important role in the folding of many proteins. A racemic synthesis of hexafluoroleucine was reported in 1968, and the first chiral synthesis of this amino acid was reported in 1998 (J. Lazar & W. A. Sheppard, 11 *J. Med. Chem.* 138 (1968); C. Zhang et al., 81 *Helv. Chem. Acta* 174 (1998)). The highest enantiomeric purity achieved in this prior work was 81% e.e. and this weakness substantially limits the value of the route for the production of hFLeu for peptide synthesis. More recently, Kumar and coworkers (X. Xing et al., 3 *Org. Lett.* 1285 (2001)) reported a ten-step synthesis of L-hFLeu from D-serine. This synthesis was reported to provide L-hFLeu in >51% yield and >99% e.e. from Garner's aldehyde, which in turn is prepared from D-Serine in five steps. This synthesis is long, difficult to reproduce, and provides material whose enantiomeric purity cannot be demonstrated using the method described. In addition, Garner's aldehyde is an expensive starting material, currently costing about $100 per g.

SUMMARY OF THE INVENTION

The present invention provides a comparatively short and efficient method for preparing L-5,5,5,5',5',5'-hexafluoroleucine (L-hFLeu) and its protected analogs from commercially available and inexpensive starting materials, including N-Cbz-L-serine. The claimed method can also be used to prepare D-hFLeu and its protected analogs by utilizing starting materials having opposite stereochemistry (e.g., N-Cbz-D-serine). Hexafluoroleucine and its protected analogs are useful for preparing fluorous peptides and proteins having known utility.

One aspect of the present invention provides a method of making a compound represented by Formula I,

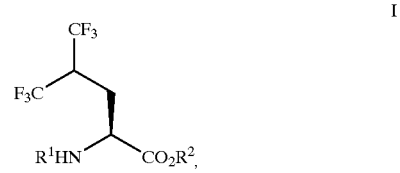

or a corresponding stereoisomer having opposite stereochemistry of Formula I, which can be represented by Formula I',

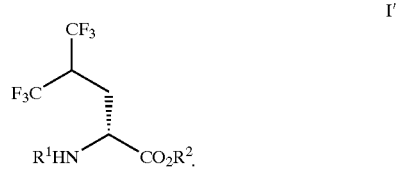

In Formula I and Formula I', $R^1$ and $R^2$ are, respectively, N-terminal and C-terminal protecting groups. The method includes providing a compound having a tertiary hydroxy group as represented by Formula IV,

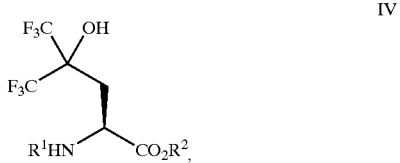

or providing a corresponding stereoisomer having opposite stereochemistry of Formula IV, and displacing the tertiary hydroxy group to yield the compound of Formula I or its corresponding stereoisomer (Formula I'). The method optionally includes de-protecting the compound of Formula I or its corresponding stereoisomer by replacing $R^1$ or $R^2$ or both $R^1$ and $R^2$ with a hydrogen atom.

Another aspect of the present invention provides a method of making the compound of Formula IV or its corresponding stereoisomer. The method includes reacting a compound of Formula III,

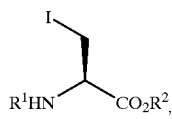

III or a corresponding stereoisomer having opposite stereochemistry of Formula III, with zinc to form an organozinc reagent, and subsequently reacting the organozinc reagent with hexafluoroacetone to yield the compound of Formula IV or its corresponding stereoisomer.

A further aspect of the present invention provides a method of making the compound of Formula I or its corresponding stereoisomer (Formula I'), which includes reacting a compound of Formula II,

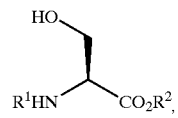

II or a corresponding stereoisomer having opposite stereochemistry of Formula II, with an iodinating agent to yield the compound of Formula III or its corresponding stereoisomer. The iodide is subsequently reacted with zinc to form an organozinc reagent, which in turn is reacted with hexafluoroacetone to form the compound of Formula IV or its corresponding stereoisomer. The compound of Formula IV and its corresponding stereoisomer have a tertiary hydroxy group, which is displaced using radical deoxygenation to yield the compound of Formula I or its corresponding stereoisomer. The method optionally includes de-protecting the compound of Formula I or its stereoisomer by replacing $R^1$ or $R^2$ or both $R^1$ and $R^2$ with a hydrogen atom.

An additional aspect of the presented invention includes synthetic intermediates, which can be used to prepare the compounds of Formula I and Formula I'. These intermediates include compounds having structures represented by Formula IV or stereoisomers having opposite stereochemistry of Formula IV.

DETAILED DESCRIPTION
Definitions and Abbreviations

Unless otherwise indicated, this disclosure uses definitions provided below. Some of the definitions and formulae may include a "—" (dash) to indicate a bond between atoms or a point of attachment to a named or unnamed atom or group of atoms. Other definitions and formulae may include an "=" to indicate a double bond.

"Alkyl" refers to straight chain and branched aliphatic hydrocarbon groups, generally having a specified number of carbon atoms (i.e., $C_{1-12}$ alkyl refers to an alkyl group having from 1 to 12 carbon atoms, inclusive). Examples of alkyl groups include, without limitation, methyl, ethyl, n-propyl, i-propyl, n-butyl, s-butyl, t-butyl, n-pentyl, s-pentyl, n-hexyl, and the like.

"Halo," "halogen" and "halogeno" may be used interchangeably, and refer to fluoro, chloro, bromo, and iodo.

Table 1 lists abbreviations used throughout the specification.

TABLE 1

List of Abbreviations

| Abbreviation | Description |
|---|---|
| Ac | acetyl |
| ACN | acetonitrile |
| AIBN | azaisobutoxycarbonyl |
| aq | aqueous |
| Boc | tert-butoxycarbonyl |
| Bn | benzyl |
| Bu | butyl |
| tert-Bu | tertiary butyl |
| DMF | dimethylformamide |
| e. e. | enantiomeric excess |
| Et | ethyl |
| EtOH | ethyl alcohol |
| Et$_2$O | ethyl ether |
| Fmoc | 9-fluoroenylmethoxycarbonyl |
| h | hour |
| hFLeu | 5,5,5,5',5',5'-hexafluoroleucine |
| D-hFLeu | (R)-5,5,5,5',5',5'-hexafluoroleucine |
| L-hFLeu | (S)-5,5,5,5',5',5'-hexafluoroleucine |
| Me | methyl |
| MeOH | methyl alcohol |
| min | minute |
| mp | melting point |
| Ph | phenyl |
| Pr | propyl |
| i-Pr | isopropyl |
| RT | room temperature (approximately 20° C. to 25° C.) |
| TFA | trifluoroacetic acid |
| THF | tetrahydrofuran |
| TLC | thin-layer chromatography |
| TMS | trimethylsilyl |

The present disclosure describes materials and methods for preparing single enantiomers of 5,5,5,5',5',5'-hexafluoroleucine (L-hFLeu and D-hFLeu), and for preparing protected analogs of L-hFLeu and D-hFLeu, which are represented by Formula I and Formula I', respectively:

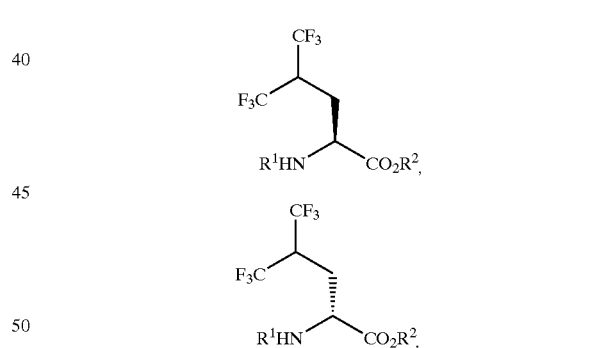

In both formulas, $R^1$ and $R^2$ are N-terminal and C-terminal protecting groups, respectively. The N-terminal protecting group prevents undesirable reaction of the amino functional group during subsequent transformations, and includes, but is not limited to, benzyl, substituted benzyl, benzyloxycarbonyl (Cbz), tert-butoxycarbonyl (Boc), 9-fluorenylmethoxycarbonyl (Fmoc), and trityl. Likewise, the C-terminal protecting group prevents undesirable reaction of the carboxy functional group and includes, but is not limited to, $C_{1-12}$ alkyl (e.g., tert-butyl) and $C_{1-12}$ haloalkyl. Particularly useful compounds of Formula I thus include N-Cbz-L-hFLeu tert-butyl ester, N-Cbz-L-hFLeu, N-Boc-L-hFLeu, L-hFLeu tert-butyl ester, N-Fmoc-L-hFLeu, N-Fmoc-L-hFLeu tert-butyl ester, and N-trityl-L-hFLeu. Likewise, particularly useful compounds of Formula I' include N-Cbz-D-hFLeu tert-butyl ester, N-Cbz-D-hFLeu, N-Boc-D-hFLeu, D-hFLeu tert-butyl ester, N-Fmoc-D-hFLeu, N-Fmoc-D-hFLeu tert-butyl ester, and N-trityl-D-hFLeu.

Scheme I shows a general method for preparing L-hFLeu and its protected analogs (Formula I) from an L-serine derivative, and employs hexafluoroacetone as a fluorocarbon source. As shown in Scheme I, the method includes providing a protected L-serine as a chiral building block (Formula II). In one useful embodiment, $R^1$ and $R^2$ of Formula II are Cbz and tert-butyl, respectively, which can be prepared by treating Cbz-L-serine with tert-butyl bromide in the presence of potassium carbonate and a phase transfer reagent, such as benzyltriethylammonium chloride. Other C-terminal and N-terminal protecting groups may be obtained using commonly employed methods of amino acid chemistry (see, e.g., M. Bodanszky & A. Bodanszky, *The Practice of Peptide Synthesis* (2d Ed. 1994).

As shown in Scheme I, the compound of Formula II is reacted with an iodinating agent in an aprotic solvent, such as dimethylformamide (DMF), at a temperature between about 20° C. and about 100° C. for about 1 h to about 24 h, to yield a compound of Formula III. Suitable iodinating agents include methyltriphenoxyphosphonium iodide, iodotriphenoxyphosphonium iodide, triphenylphosphine-N-iodosuccinimide, triphenylphosphine-tetraiodomethane, triphenylphosphine-2,4,5-triiodoimidazole, a mixture of triphenylphosphine, iodine, and imidazole, and the like. A particularly useful iodinating agent is methyltriphenoxyphosphonium iodide.

Following iodination, the compound of Formula III is reacted with zinc dust in an aprotic solvent (e.g., DMF) and in the presence of a catalyst (e.g., CuBr SMe$_2$) to form an organozinc reagent, which is subsequently reacted in-situ with hexafluoroacetone gas at a temperature between about −30° C. and about −25° C. to yield, upon work up, a compound having the requisite fluorinated carbon skeleton (Formula IV).

As shown in Scheme I, the compound of Formula IV includes a tertiary hydroxy group that is subsequently displaced by a hydrogen atom, yielding a protected L-hFLeu compound (Formula I). A useful technique for displacing the tertiary hydroxy group includes radical deoxygenation, in which the hydroxy group is converted to an oxalyl ester, a thionocarbonate, or a dithiocarbonate by treatment with an oxalyl chloride, a chlorothionoformate, or a chlorodithioformate, usually in the presence of base, such as pyridine. Suitable oxalyl chlorides, chlorodithioformates, and chlorothionoformates include phenyl and methyl oxalyl chloride, phenyl chlorodithioformate, and phenoxy, 2,4,6-trichlorophenoxy, 4-fluorophenoxy, pentafluorophenoxy and thiophenoxy chlorothionoformate.

The resulting oxalyl ester, thionocarbonate, or dithiocarbonate is subsequently treated with a source of hydrogen radicals in the presence of a radical initiator, to afford the compound of Formula I. Although trialkyltin hydrides, such as tributyltin hydride, are a good source of hydrogen radicals, other useful sources include triphenylsilane, diphenylsilane, dialkylphosphite, as well as salts of hypophosphorous acid. Suitable radical initiators include azaisobutyronitrile (AIBN). For a discussion of radical deoxygenation, see, e.g., D. H. R. Barton & H. W. McCarobie, I *J. Chem. Soc. Perkin Trans.* 1, 1574 (1975); M. J. Robins & J. S. Wilson 103 *J. Am. Chem. Soc.* 933 (1981); M. J. Robins & J. S. Wilson, 105 *J. Am. Chem. Soc.* 4059 (1983); S. C. Dolan and J. MacMillan, *J. Chem. Soc. Chem. Comm.* 1588 (1985).

As shown in Scheme I, the amino, carboxy or amino and carboxy groups may be de-protected by displacing $R^1$ (Formula VI) or $R^2$ (Formula V) or both $R^1$ and $R^2$ (L-hFLeu) using conventional techniques. For example, if $R^1$ and $R^2$ are, respectively, Cbz and tert-butyl, the carboxy functional group can be de-protected by treating the compound of Formula I with trifluoroacetic acid (TFA) in an aprotic solvent (e.g., dichloromethane). Additionally, the amino functional group can be de-protected by treating the compound of Formula I with hydrogen in the presence of a Pd catalyst or by treating the compound of Formula I with HBr and acetic acid. Similarly, $R^1$ can be displaced from the compound of Formula V to yield L-hFLeu. Though not shown in Scheme I, $R^1$ can be displaced earlier in the process by treating the compound of Formula IV with hydrogen.

In addition to preparing L-hFLeu and its protected analogs (Formula I), the method depicted in Scheme I can be used to prepare D-hFLeu and protected analogs (Formula I') by utilizing starting materials having opposite stereochemistry (i.e., a D-serine derivative). Thus, for example, Cbz-D-serine may be treated with tert-butyl bromide in the presence of potassium carbonate and a phase transfer reagent to yield a protected D-serine, which is subsequently reacted with an iodinating agent. The resulting iodide is reacted with zinc to form an organozinc reagent, which in turn is reacted with hexafluoroacetone to generate a compound having a tertiary hydroxy group that is subsequently displaced using radical deoxygenation to yield N-Cbz-D-hFLeu tert-butyl ester. De-protecting the amino and caroboxy functional groups gives D-hFLeu.

Scheme I

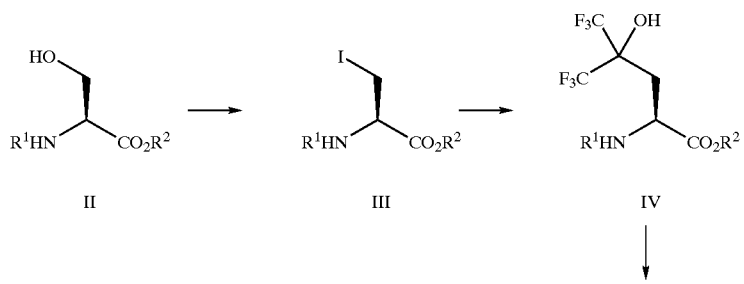

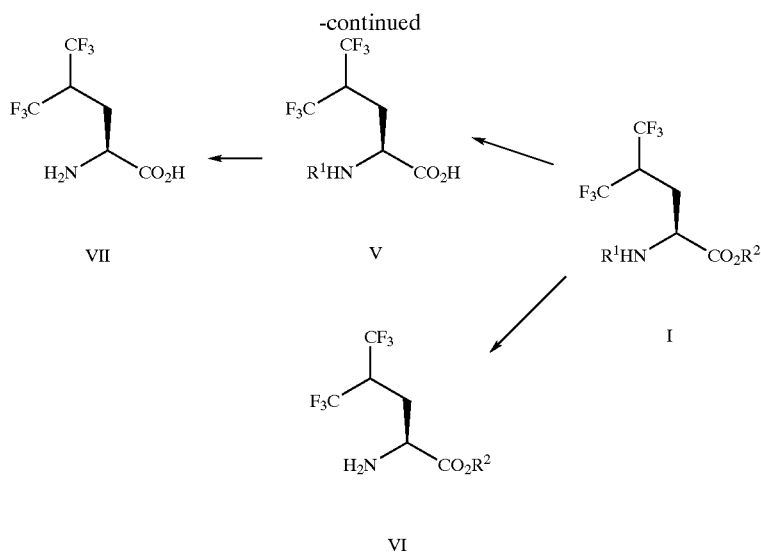

EXAMPLES

The following examples are intended as illustrative and non-limiting, and represent specific embodiments of the present invention.

Example 1

Preparation of 2-benzyloxycarbonylamino-3-hydroxy-propionic acid tert-butyl ester (Formula II, $R^1$=Cbz, $R^2$=tert-butyl)

A mixture of Cbz-L-serine (10.0 g, 42 mmol), benzyltriethylammonium chloride (9.5 g, 42 mmol) and potassium carbonate (38.0 g, 275 mmol) in $CH_3CN$ (80 mL) was stirred vigorously for 5 h at RT. 2-Bromo-2-methyl propane was added and the reaction mixture was warmed to 45–50° C. and stirred rapidly. The reaction mixture became very thick after 2–3 h. Additional $CH_3CN$ was added (50 mL) to facilitate stirring and the resulting reaction mixture was stirred for 24 h. The reaction mixture was then cooled to RT and most of the $CH_3CN$ was removed by rotary evaporation. The reaction mixture was then partitioned between ethyl acetate (200 mL) and water (100 mL). The aqueous layer was extracted with ethyl acetate (3×100 mL). The ethyl acetate layers were combined and washed with water (100 mL), then with sat. aq. NaCl solution (2×100 mL), and then dried over $Na_2SO_4$, filtered and concentrated. If the product did not crystallize upon concentration, it was triturated with hexanes and filtered to give 2-benzyloxycarbonylamino-3-hydroxy-propionic acid tert-butyl ester as a white solid (10.0 g, 81% yield).

Example 2

Preparation of 2-benzyloxycarbonylamino-3-iodo-propionic acid tert-butyl ester (Formula III, $R^1$=Cbz, $R^2$=tert-butyl)

Methyltriphenoxyphosphonium iodide (($PhO)_3PMeI$), 17.09 g, 40 mmol) was added to a DMF (67 mL) solution of 2-benzyloxycarbonylamino-3-hydroxy-propionic acid tert-butyl ester at RT. The resulting solution was stirred at RT for 3.5 h. The reaction mixture was cooled to 0° C. (ice bath) and stirred vigorously. Solid $NaHCO_3$ (10 g) was added followed by the addition of water (20 mL) over a period of 5 min. The reaction mixture was then partitioned between water (250 mL) and 1:1 $Et_2O$-hexanes (250 mL). The aqueous layer was extracted twice with 1:1 $Et_2O$-hexanes (100 mL). The organic layers were combined and washed with aq. NaOH (0.05 M, 200 mL portions) until all of the phenol was removed (as judged by TLC using 35% EtOAc-hexanes). The organic layer was further washed with sat. aq. NaCl (100 mL) and then dried over $Na_2SO_4$, filtered, and concentrated. The crude product was purified by column chromatography using 20% EtOAc-hexanes to give 2-benzyloxycarbonylamino-3-iodo-propionic acid tert-butyl ester as a clear oil that crystallized upon standing in the refrigerator (4° C.) into a white solid (9.19 g, 85% yield). $R_f$ 0.59 (30% EtOAc-hexanes); mp 34–36° C.; $^1$H-NMR (300 MHz, $CDCl_3$): δ 7.40–7.30 (5H), 5.62 (br d, J=6.9 Hz, 1H), 5.19–5.05 (2H), 4.42 (ddd, J=7.1, 7.1, 3.6 Hz, 1H), 3.59 (d, J=3.6 Hz, 2H), 1.50 (s, 9H); $^{13}$C-NMR (100 MHz, $CDCl_3$): δ 168.1, 155.4, 136.0, 128.5, 128.2, 128.1, 83.5, 67.1, 54.0, 27.9, 8.4.

Example 3

Preparation of 2-benzyloxycarbonylamino-5,5,5-trifluoro-4-hydroxy-4-trifluoromethyl-pentanoic acid tert-butyl ester (Formula IV, $R^1$=Cbz, $R^2$=tert-butyl)

Zinc dust (15 g, 230 mmol) in a 3-neck flask (250 mL) was heated under vacuum (1 mm Hg) using a heat gun for 5 min (the flask was hot to the touch) and then allowed to cool to RT. The flask was then purged twice with dry nitrogen. Dry DMF (38 mL) was added and the resulting mixture was warmed to ca. 50° C. using a heat gun and stirred vigorously. 1,2-Dibromoethane (1.0 mL, 12 mmol) was added and the resulting mixture was allowed to cool to RT and stirred vigorously for 30 min. Trimethylsilyl chloride (TMS-Cl) (0.3 mL, 2 mmol) was then added and the resulting mixture stirred vigorously for another 30 min. A dry DMF solution (38 mL) of 2-benzyloxycarbonylamino-3-iodo-propionic acid tert-butyl ester (23.21 g, 57 mmol) was then added over a period of 5 min and was consumed after 45 min (TLC, 40% $Et_2O$-hexanes, ninhydrin). In another 3-neck flask (250 mL), $CuBr.SMe_2$ was heated under vacuum (1 mm Hg) using a heat gun until a light green color appeared (ca. 5 min). The light green solid was allowed to cool to RT, and then dry DMF (10 mL) was added. The DMF solution of the organozinc reagent was transferred to the CuBr/DMF mixture, leaving behind most of the unreacted zinc. The zinc was rinsed with DMF (10 mL) and then the DMF portion was transferred as before making sure that most of the zinc was left behind. The resulting DMF solution of the organozinc reagent and CuBr was cooled between −20° C. and −30° C. and stirred rapidly. Hexafluoroacetone gas (15.2 g, 92 mmol) was slowly bubbled into the reaction mixture (ca. 10–15 min) via a needle (6", 20 ga.). Other experiments have shown that only a stoichiometric amount of hexafluoroacetone is needed. The resulting mixture was stirred rapidly between −20° C. and −30° C. for 2 h and then warmed to RT overnight. Water (100 mL) was added followed by 1 M aq. HCl until pH=4. The reaction mixture was then poured into water (300 mL) and EtOAc (200 mL). The aq. layer was extracted with EtOAc (3×150 mL). The EtOAc layers were combined and washed with 1:1 water-saturated aq. NaCl (3×100 mL), sat. aq. NaCl (2×100 mL), then dried over $Na_2SO_4$, filtered, and concentrated to give 2-benzyloxycarbonylamino-5,5,5-trifluoro-4-hydroxy-4-trifluoromethyl-pentanoic acid tert-butyl ester as a white solid (23.96 g, 94% yield), which did not require purification. $R_f$ 0.49 (40% $Et_2O$-hexanes); mp 83–89° C.; $^1$H-NMR (400 MHz, $CDCl_3$): δ 7.50 (br s, 1H), 7.40–7.32 (5H), 6.00 (br s, 1H), 5.13 (dd, J=16.1, 12.1 Hz, 2H), 4.44 (app dd, J=4.8, 4.4 Hz, 1H), 2.74 (dd, J=16.1, 4.4 Hz, 1H), 2.24 (ddd, J=16.1, 4.8, 1.1 Hz, 1H), 1.51 (s, 9H); $^{13}$C-NMR (100 MHz, $CDCl_3$): δ 169.9, 157.1, 135.3, 128.62, 128.58, 128.4, 128.3, 123.1 (q, $J_{CF}$=286.8 Hz), 84.6, 74.9 (quintet, $J_{CCF}$=29.4 Hz), 68.0, 48.9, 35.7, 27.7; $^{19}$F-NMR (376.3 MHz, $CDCl_3/C_6F_6$): δ 85.1–84.7, 83.6–83.2; HRMS-FAB (m-nitrobenzyl alcohol, m/z): [M+Na]$^+$ calculated for $C_{18}H_{21}NO_5F_6Na$, 468.1222; found, 468.1229.

Example 4

Preparation of N-Cbz L-5,5,5,5',5',5'-hexafluoroleucine tert-butyl ester (Formula I, $R^1$=Cbz, $R^2$=tert-butyl)

Dry pyridine (0.73 mL, 9.0 mmol) was added drop wise to a rapidly stirred dry toluene (15.7 mL) solution of 2-benzyloxycarbonylamino-5,5,5-trifluoro-4-hydroxy-4-trifluoromethyl-pentanoic acid tert-butyl ester (3.493 g, 7.85 mmol) and phenyl oxalyl chloride (1.738 g, 9.42 mmol) at RT. The resulting mixture was stirred rapidly for 3 h, whereupon a white precipitate (pyridinium chloride) was formed. The reaction mixture was filtered through cotton to remove the precipitate. The filtrate was concentrated using rotary evaporation to azeotrope most of the excess pyridine. The resulting crude oxalate ester and AIBN (0.575 g, 2.35 mmol) were dissolved in dry toluene (15.7 mL) and then added drop wise to a rapidly stirred toluene (15.7 mL) solution of $Bu_3SnH$ (3.22 mL, 11.9 mmol) at 100° C. (oil bath) over a period of 5 min. The resulting solution was stirred at this temperature for 1 h and then cooled to RT. Ether (20 mL) was added followed by a KF-Celite® mixture (ca. 10 g, to remove organotin compounds) and the resulting mixture was stirred vigorously for 2 h. The solvent was decanted and the KF-Celite® residue was washed with ether (2×20 mL). The solvent was removed and the resulting residue was purified by column chromatography using 13% $Et_2O$-hexanes to give N-Cbz L-5,5,5,5',5',5'-hexafluoroleucine tert-butyl ester as a clear oil that solidified to a translucent, moist solid (2.829 g, 84% yield). $R_f$ 0.59 (40% $Et_2O$-hexanes); mp 43–45° C.; $^1$H-NMR (400 MHz, $CDCl_3$): δ 7.40–7.32 (5H), 5.39 (br d, J=5.3 Hz, 1H), 5.13 (s, 2H), 4.45–4.38 (1H), 3.38–3.22 (1H), 2.40–2.28 (1H); $^{13}$C-NMR (100 MHz, $CDCl_3$): δ 169.6, 156.2, 135.9, 128.5, 128.3, 128.2, 83.6, 67.3, 52.4, 44.5 (quintet, $J_{CCF}$=28.4 Hz), 27.8; $^{19}$F-NMR (376.3 MHz, $CDCl_3/C_6F_6$): δ 94.29–94.14, 94.08–93.90; HRMS-Cl ($NH_3$, m/z): [M+$NH_4$]$^+$ calculated for $C_{18}H_{25}N_2O_4F_6$, 447.1719; found, 447.1715.

Example 5

Preparation of L-5,5,5,5',5',5'-hexafluoroleucine (Formula VII)

TFA (16 mL, 210 mmol) was added to a solution of N-Cbz L-5,5,5,5',5',5'-hexafluoroleucine tert-butyl ester (8.97 g, 21 mmol) at 0° C. in $CH_2Cl_2$ (12 mL) and the resulting mixture was stirred for 1 h and then allowed to warm to RT over a period of 3 h. The solvent was removed using rotary evaporation. The crude product was dissolved in toluene (50 mL) and concentrated to remove most of the remaining TFA; this process was repeated 3 times. The crude product (Formula V, $R^1$=Cbz) was dissolved in MeOH (100 mL) and 10% Pd/C (0.8 g) was added. The reaction mixture was stirred vigorously overnight under an atmosphere of $H_2$. MeOH (75 mL) was added to dissolve the precipitated product and then $N_2$ was bubbled through the reaction mixture for 15 min. The reaction mixture was filtered through Celite® and concentrated. The crude product was washed with $Et_2O$ (300 mL) to give L-5,5,5,5',5',5'-hexafluoroleucine as a light gray solid (4.62 g, 92% yield, 96% e.e., Mosher amide). Recrystallization from MeOH gave compound L-5,5,5,5',5',5'-hexafluoroleucine as white needles (99% e.e., Mosher amide). $^1$H-NMR (400 MHz, $CD_3OD$): δ 4.29–4.16 (1H), 3.67 (dd, J=9.9, 5.9 Hz, 1H), 2.37–2.28 (1H), 2.24–2.15 (1H); $^{19}$F-NMR (376 MHz, $CD_3OD/C_6F_6$): δ 96.6 (quintet, J=9.2 Hz), 95.9 (quintet, J=9.2 Hz); $[α]_D^{22}$=+9.3° (c 0.7, MeOH); HRMS-FAB (m-nitrobenzyl alcohol, m/z): [M+H]$^+$ calculated for $C_6H_8NO_2F_6$, 240.0459; found, 240.0461.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, granted patents, and publications, are incorporated herein by reference in their entirety and for all purposes.

What is claimed is:

1. A compound of Formula IV,

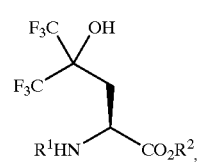

or a corresponding stereoisomer having opposite stereochemistry of Formula IV, wherein $R^1$ and $R^2$ are, respectively, N-terminal and C-terminal protecting groups.

2. The compound of claim 1, wherein $R^1$ is benzyl, substituted benzyl, Cbz, Boc, Fmoc, or trityl, and $R^2$ is alkyl or haloalkyl.

3. A method of making a compound of claim 1, the method comprising:

reacting a compound of Formula III,

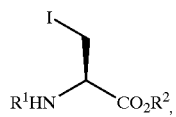

III or a corresponding stereoisomer having opposite stereochemistry of Formula III, with zinc to form an organozinc derivative; and reacting the organozinc derivative with hexafluoroacetone to yield the compound of Formula IV or the corresponding stereoisomer, wherein $R^1$ and $R^2$ in Formula III are as defined in Formula IV.

4. The method of claim 3, wherein $R^1$ in Formula III and Formula IV is benzyl, substituted benzyl, Cbz, Boc, Fmoc, or trityl, and $R^2$ is alkyl or haloalkyl.

5. The method of claim 3, wherein $R^1$ in Formula III and Formula IV is Cbz.

6. The method of claim 3, wherein $R^2$ in Formula III and Formula IV is tert-butyl.

* * * * *